United States Patent [19]

Seidel et al.

[11] 4,269,829

[45] May 26, 1981

[54] METHOD AND COMPOSITION FOR TREATING HELMINTHS CONTAINING O,O-DIALKYL-N-(SUBSTITUTED PHENYL)AMINOTHIOCARBONYL PHOSPHORAMIDATES

[75] Inventors: Michael Seidel, Chalfont; W. David Weir, Levittown; Martha H. Wolfersberger, Perkasie, all of Pa.

[73] Assignee: Rohm and Haas Company, Philadelphia, Pa.

[21] Appl. No.: 49,849

[22] Filed: Jun. 18, 1979

[51] Int. Cl.³ .......................... A61K 31/66; C07F 9/24
[52] U.S. Cl. ..................................... 424/211; 260/938
[58] Field of Search ......................... 260/938; 424/211

[56] References Cited

U.S. PATENT DOCUMENTS

| 3,384,683 | 5/1968 | Schwarze | 260/938 |
| 3,393,253 | 7/1968 | Wiesboeck | 260/938 |
| 3,476,837 | 11/1969 | Addor | 260/938 |
| 3,887,657 | 6/1975 | Battershell et al. | 260/938 |
| 3,957,924 | 5/1976 | Meyer et al. | 260/938 |
| 4,076,809 | 2/1978 | Weir et al. | 424/211 |
| 4,139,614 | 2/1979 | Kilboarn et al. | 424/211 |

FOREIGN PATENT DOCUMENTS

| 1139494 | 11/1962 | Fed. Rep. of Germany | 260/938 |
| 2114885 | 10/1972 | Fed. Rep. of Germany | 260/938 |
| 2260716 | 5/1974 | Fed. Rep. of Germany | 260/959 |

*Primary Examiner*—Anton H. Sutto
*Attorney, Agent, or Firm*—Terence P. Strobaugh; George W. F. Simmons

[57] ABSTRACT

Phosphoramidates and salts and salt complexes useful as anthelmintics are disclosed. The products are prepared by treating an aminobenzene with an appropriately substituted isothiocyanatoate.

3 Claims, No Drawings

METHOD AND COMPOSITION FOR TREATING HELMINTHS CONTAINING O,O-DIALKYL-N-(SUBSTITUTED PHENYL)AMINOTHIOCARBONYL PHOSPHORAMIDATES

FIELD OF THE INVENTION

This invention relates to phosphoramidates and salts and salt complexes, to processes for making such compounds, to methods of treating helminth infections and to anthelmintic compositions containing them.

DESCRIPTION OF THE PRIOR ART

There are numerous patents describing phosphoramidates and salts thereof including U.S. Pat. Nos. 4,139,614; 3,957,924; 3,393,253; 3,384,683; 3,476,837; 3,887,657; and 3,975,522; German Pat. Nos. 1,139,494; 2,114,885; 957,712 and 2,260,719. However none of these patents disclose or suggest the compounds of this invention.

An object of this invention is to provide a new class of phosphoramidates (I, infra), methods for preparing these compounds, compositions containing said compounds and to their use as anthelmintic agents.

The novel phosphoramidates (I, infra) of this invention have the following structural formula:

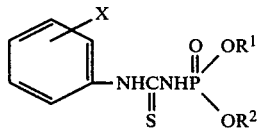

$R^1$ and $R^2$ is the same or different group selected from alkyl for example lower alkyl of from 1 to 6 carbon atoms such as methyl, ethyl, n-propyl, iso-propyl, n-butyl, iso-butyl, tert-butyl, pentyl, hexyl and the like; and X is phenylthio, phenylsulfinyl, phenylsulfonyl, phenoxy or styryl and the agronomically acceptable metal salts and metal salt complexes thereof.

When compounds of General Formula I can exist in various isomer and stereoisomer forms all such isomers and their mixtuures and racemates are includes within the scope of this present invention.

PREFERRED EMBODIMENT

A preferred embodiment of this invention relates to the 2-substituted phosphoramidates (Ia, supra) of the following structural formula:

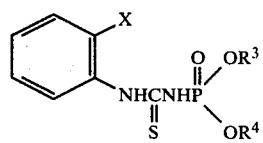

X is as defined above; $R^3$ and $R^4$ are lower alkyl of from 1 to 4 carbon atoms and zinc salts and zinc metal complexes thereof. These compounds exhibit particularly good anthelmintic activity.

The phosphoramidates (I, supra) of this invention are prepared by treating the corresponding 2-amino-substituted benzene deriv. (II, infra) with an appropriately substituted isothiocyanatoate. The reaction may be conducted at a temperature in the range of from 0° C. to 60° C. for a period of time from a few minutes to about three hours. Any solvent in which the reactants are reasonably soluble and substantially inert may be employed. Suitable solvents include dimethyl formamide (DMF), acetone, diethyl ether, 1,2-dimethoxy ethane and the like. The following equation illustrates this process:

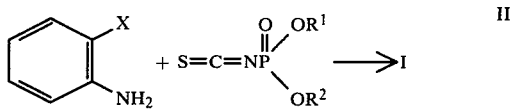

wherein $R^1$, $R^2$ and X are as defined above.

The metal salts of this invention are the alkali metal, alkaline earth metal and transition metal salts of the compounds of Formula I. The preferred metal salt is the zinc salt.

The metal salt complexes of this invention can be represented by the following formula which is presented for illustrative purposes only:

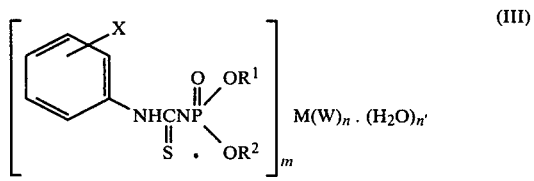

wherein $R^1$, $R^2$, and X are as defined above, M is a metal cation which can be selected from Groups IIA, IIIA, IB, IIB, VIIB and VIII of the Periodic Table; W is an anion such as chloride, bromide, iodide, sulfate, bisulfate, phosphate, nitrate, perchlorate, carbonate, bicarbonate, hydroxide, acetate, oxalate, malate, citrate and the like; m is an integer of 1-2; n is an integer of 1 to 3; and n' is an integer of 0-4.

Among the compounds depicted by Formula III above, the preferred compounds are those wherein the metal cation is a transition metal such as copper, zinc, nickel, cobalt, tin, cadmium, or manganese; or an alkaline earth metal such as calcium or magnesium and wherein the anion is chloride, bromide, nitrate, sulfate or hydroxide. The most preferred salts are those wherein the metal cation is copper, zinc, nickel, cobalt, tin, cadmium or manganese, and the anion is hydroxide.

The alkali and alkaline earth metal salts of this invention are prepared by (1) adding an alkali or alkaline earth metal hydroxide or hydride to a suspension of the phosphoramidate in a suitable solvent, (2) stirring the mixture until a solution forms, and (3) freeze drying the solution, or in the alternative, (4) concentrating the solution in vacuo at room temperature and drying the residue in a vacuum oven at room temperature.

The metal salt complexes and transition metal salts are prepared in substantially the same manner varying the molar ratios of the metal salt employed by (1) reacting, in an aqueoous or alcoholic medium an alkali metal salt of a phosphoramidates of this invention, with a metal salt selected from Group IIA, IIIA, IB, IIB, VIIB, or VIII of the Periodic Table, (2) filtering off the precipitate which forms, and (3) washing and drying the precipitate to give the product. This method is more fully described in U.S. Pat. No. 4,139,614.

The phosphoramidates of Formula I are anthelmintics and have broad spectrum activity against parasites of animals especially warm blooded animals, including both mature and immature parasitic forms. In particular, these compounds exhibit high activity against various helmintic infections of the intestinal tract of economically important animals, coupled with low systemic toxicity to the host animal.

For example, the disclosed compounds are generally effective in clearing mice of worm infections for laboratory purposes, among others: *Syphacia obvelata* or Aspilcularis tetraptera (mouse pinworm), the migratory stages of *Ascaris suum, Hymenolepsis nana* and *Nematospiroides dubius*.

Animals of low weight are treated with unit doses ranging no higher than a few milligrams; whereas, animals of higher body weight, require proportionately larger unit doses ranging up to several grams. Preferably, a single dose is administered for each animal species based on the weight of that species.

The amount of ingredient administered will depend on the weight of the host, but will usually be a unit dosage between about 1 mg./kg. and 125 mg./kg. of body weight. It is contemplated that dosage units containing the compounds of Formula I of this invention as the essentially active ingredient will be administered, orally or by injection, in the treatment and control of helmintic infections in domestic animals such as sheep, cattle, horses, dogs, cats, fish, swine and goats and also in man.

When used as an anthelmintic agent for the treatment and/or prevention of helminthiasis, the novel compounds of Formula I of this invention may be administered orally in a unit dosage form such as a paste, gel, capsule, bolus, tablet or as a liquid drench. They may also be administered orally by intimately dispersing them in an animal feedstuff or by using them as a top dressing or in the form of pellets which are added to a finished feed. Alternatively, they may be administered to animals in a liquid carrier vehicle by intraruminal, intramuscular and intratracheal injection. The quantity of active material required to give best anthelmintic response will depend upon the particular compound employed, the species of animal to be treated and the type and severity of helminth infection. Good results are usually obtained when there is administered a total dose of from about 1 to about 125 mg. of active ingredient per kg. of animal body weight. Such total dose may be given at one time or in divided doses over a short period of time such as 1 to 2 days.

The following examples illustrate the compounds of this invention and the methods by which they are prepared. However, the examples are illustrative only and it will be apparent to those having ordinary skill in the art that all of the products embraced by Formula I, supra, may also be prepared in an analogous manner by substituting the appropriate starting materials for those set forth in the examples.

EXAMPLE 1

O,O-Diethyl-N-(2-phenoxyphenyl)aminothiocarbonyl phosphoramidate

To a solution of 1.3 g. (0.007 mol) 2-phenoxyaniline in 10 ml. of acetone there is added 1.4 g. (0.007 mol) of O,O-diethyl phosphoroisothiocyanatoate. The solution is diluted with water, made basic with 50% aqueous sodium hydroxide, and extracted with ether. The aqueous layer is acidified with concentrated hydrochloric acid and extracted with methylene dichloride. The methylene dichloride solution is concentrated in vacuo to afford 1.8 g. (66.7% yield) of product that crystallizes upon standing, mp. 100°–103° C.

Elemental analysis for $C_{17}H_{21}N_2O_4PS$: Calc. C 53.67 H 5.56 N 8.14 P 8.43; Found C 54.11 H 5.64 N 8.12 P 9.05; 53.90, 5.64

EXAMPLE 2

Zinc salt of O,O-Diethyl-N-(2-phenoxyphenyl)aminothiocarbonyl phosphoramidate

Step A—Sodium salt of O,O-Diethyl-N-(2-phenoxyphenyl)aminothiocarbonylphosphoramidate To a slurry of 2.9 g. (0.0076 mol) O,O-diethyl-N-(2-phenoxyphenyl)aminothiocarbonyl phosphoramidate in 50 ml of deionized water there is added 0.6 g. (0.0076 mol) of 50% aqueous sodium hydroxide to afford sodium salt of O,O-diethyl-N-(2-phenoxyphenyl)aminothiocarbonyl-phosphoramidate.

Step B—Zinc salt of O,O-diethyl-N-(2-phenoxyphenyl)aminothiocarbonyl phosphoramidate The mixture is stirred until a clear solution is formed and to it there is added a solution of 0.5 g. (0.0038 mol) zinc chloride in 10 ml of deionized water. The "gummy" suspension formed is stirred at room temperature for 18 hrs. and to it there is added 0.5 g. (0.0038 mol) of zinc chloride dissolved in 10 ml of deionized water. The water is decanted and the "gummy precipitate" is slurried in methanol. The slurry is vacuum filtered and the filter cake dried to afford 1.6 g. (26% yield) of product, mp. 90°–92° C.

Elemental analysis for $C_{34}H_{40}N_4O_8P_2S_2Zn$: Calc. C 49.55 H 4.89 N 6.80 P 7.78 Zn 7.93; Found C 48.38 H 4.86 N 7.09 P 7.88 Zn 7.48

EXAMPLE 3

O,O-Diethyl-N-(2-thiophenoxyphenyl)aminothiocarbonyl phosphoramidate

To a solution of 2.0 g. (0.01 mol) 2-thiophenoxyaniline in 50 ml. of diethyl ether there is added 2.0 g. (0.01 mol) of O,O-diethyl phosphoroisothiocyanatoate. The mixture is allowed to stand at room temperature for 2 hrs. and the diethyl ether is allowed to evaporate. The residue is dissolved in diethyl ether and to it there is added hexane. The oil that separates is isolated, washed with several portions of hexane and allowed to stir in hexane for 18 hrs. The crystalline precipitate that is formed is isolated by vacuum filtration and dried to afford 1.6 g. (40.4% yield) of product, mp. 97°–100° C.

Elemental analysis for $C_{17}H_{21}N_2O_3PS_2$: Calc.: C 51.50 H 5.34 N 7.07 P 7.81 S 16.17; Found: C 51.44 H 5.39 N 7.22 P 7.56 S 15.94

By substituting 2-phenylsulfinylaniline and 2-phenylsulfonylaniline for the 2-thiophenoxy aniline in Example 3 and by following substantially the same procedure there is obtained O,O-diethyl-N-(2-phenylsulfinylphenyl)aminothiocarbonyl phosphoramidate, and O,O-diethyl-N-(2-phenylsulfonylphenyl)aminothiocarbonyl phosphoramidate, respectively.

EXAMPLE 4

O,O-Diethyl-N-(2-styrylphenyl)aminothiocarbonyl phosphoramidate

To a stirred solution of 3.4 g. (0.01 mol) 2-aminostilbene in 20 ml of acetone there is added 2.0 g. (0.01 mole) of O,O-diethyl phosphoroisothiocyanatoate. The mixture is stirred at room temperature for 2 hrs. and is concentrated in vacuo. The concentrate is crystallized with ethyl acetate and the crystals are isolated to afford 0.4 g. (5% yield) of product, mp. 124°–126° C. The ethyl acetate filtrate is concentrated in vacuo and the concentrate is treated with diethyl ether to afford an additional 1.2 g. of product (38% overall yield).

Elemental analysis for $C_{19}H_{23}N_2O_3PS_2$: Calc.: C 58.45 H 5.94 N 7.18 P 7.93 S 8.21; Found: C 58.60 H 5.85 N 6.99 P 5.63 S 9.38

The compositions of this invention can be utilized as the sole anthelmintic or they can be employed in conjunction with other anthelmintics.

Many variations of this invention are possible without departing from the spirit or scope thereof.

We claim:

1. A compound named O,O-diethyl-N-(2-styrylphenyl)-aminothiocarbonyl phosphoramidate.
2. A method for treating helminths which comprises the administration of an effective amount of the compound of claim 1.
3. A composition useful in the treatment of helminths which comprises the unit dosage between about 1 milligram per kilogram and 125 milligrams per kilogram of body weight of the compound of claim 1.

* * * * *